United States Patent
Stevenson et al.

(10) Patent No.: US 8,160,705 B2
(45) Date of Patent: Apr. 17, 2012

(54) SHIELDED RF DISTANCE TELEMETRY PIN WIRING FOR ACTIVE IMPLANTABLE MEDICAL DEVICES

(75) Inventors: Robert A. Stevenson, Canyon Country, CA (US); Christine A. Frysz, Marriottsville, MD (US); Haytham Hussein, Woodstock, MD (US); Richard L. Brendel, Carson City, NV (US)

(73) Assignee: Greatbatch Ltd, Clarence, NY (US)

( * ) Notice: Subject to any disclaimer, the term of this patent is extended or adjusted under 35 U.S.C. 154(b) by 808 days.

(21) Appl. No.: 11/307,306

(22) Filed: Jan. 31, 2006

(65) Prior Publication Data
US 2007/0043399 A1    Feb. 22, 2007

Related U.S. Application Data

(60) Provisional application No. 60/594,236, filed on Mar. 22, 2005, provisional application No. 60/655,853, filed on Feb. 23, 2005.

(51) Int. Cl.
*A61N 1/00* (2006.01)
*H03L 5/00* (2006.01)

(52) U.S. Cl. ............... 607/32; 607/37; 333/182

(58) Field of Classification Search ............ 607/32, 607/37; 331/182
See application file for complete search history.

(56) References Cited

U.S. PATENT DOCUMENTS

| | | | |
|---|---|---|---|
| 4,148,003 A | 4/1979 | Colburn et al. | |
| 4,424,551 A | 1/1984 | Stevenson et al. | |
| 5,333,095 A | 7/1994 | Stevenson et al. | |
| 5,751,539 A | 5/1998 | Stevenson et al. | |
| 5,896,267 A | 4/1999 | Hittman et al. | |
| 5,905,627 A * | 5/1999 | Brendel et al. | 361/302 |
| 5,959,829 A | 9/1999 | Stevenson et al. | |
| 5,973,906 A | 10/1999 | Stevenson et al. | |
| 5,978,204 A | 11/1999 | Stevenson | |
| 5,994,975 A * | 11/1999 | Allen et al. | 333/26 |
| 6,008,980 A | 12/1999 | Stevenson et al. | |
| 6,052,623 A * | 4/2000 | Fenner et al. | 607/36 |
| 6,240,317 B1 | 5/2001 | Villaseca et al. | |
| 6,275,369 B1 | 8/2001 | Stevenson et al. | |
| 6,529,103 B1 | 3/2003 | Brendel et al. | |
| 6,566,978 B2 * | 5/2003 | Stevenson et al. | 333/182 |
| 6,643,903 B2 | 11/2003 | Stevenson et al. | |
| 6,765,779 B2 | 7/2004 | Stevenson et al. | |
| 6,765,780 B2 | 7/2004 | Brendel et al. | |
| 6,888,715 B2 * | 5/2005 | Stevenson et al. | 361/302 |
| 6,901,292 B2 | 5/2005 | Hrdlicka et al. | |

(Continued)

FOREIGN PATENT DOCUMENTS
WO    WO9741923    11/1997

*Primary Examiner* — Nicole F Lavert
(74) *Attorney, Agent, or Firm* — Michael F. Scalise

(57) ABSTRACT

In an electromagnetic interference (EMI) filter terminal for an active implantable medical device (AIMD), an insulated and shielded RF telemetry pin is provided to prevent re-radiation of unwanted stray signals, including the telemetry signal itself, to adjacent sensitive circuits or lead wires. The invention provides for an EMI filter terminal assembly for an AIMD including a radio frequency (RF) telemetry pin antenna extending therethrough. The RF telemetry pin antenna includes a conductive shield extending over a portion of the RF telemetry pin antenna in non-conductive relation with the telemetry pin, and conductively connected to a ground associated with the AIMD. The assembly may also include an insulation tube between the RF telemetry pin antenna and the conductive shield covering a portion of the RF telemetry pin antenna.

25 Claims, 14 Drawing Sheets

U.S. PATENT DOCUMENTS

| | | |
|---|---|---|
| 6,999,818 B2 | 2/2006 | Stevenson et al. |
| 7,016,733 B2 * | 3/2006 | Dublin et al. ............... 607/36 |
| 7,038,900 B2 * | 5/2006 | Stevenson et al. ......... 361/302 |
| 7,046,499 B1 * | 5/2006 | Imani et al. ................ 361/302 |
| 7,175,482 B2 * | 2/2007 | Zart et al. .................. 439/736 |
| 7,260,434 B1 * | 8/2007 | Lim et al. ..................... 607/37 |
| 7,303,422 B2 * | 12/2007 | Hoffer et al. .............. 439/359 |
| 7,327,553 B2 * | 2/2008 | Brendel ...................... 361/302 |
| 2004/0015200 A1 * | 1/2004 | Lofstedt ...................... 607/37 |
| 2004/0147974 A1 | 7/2004 | Engmark et al. |
| 2004/0215280 A1 * | 10/2004 | Dublin et al. .............. 607/36 |
| 2004/0260354 A1 * | 12/2004 | Nielsen et al. ............. 607/37 |
| 2005/0007718 A1 * | 1/2005 | Stevenson et al. ......... 361/118 |
| 2005/0248907 A1 * | 11/2005 | Stevenson et al. ...... 361/306.2 |
| 2006/0009813 A1 | 1/2006 | Taylor et al. |
| 2006/0167522 A1 * | 7/2006 | Malinowski ................ 607/37 |

* cited by examiner

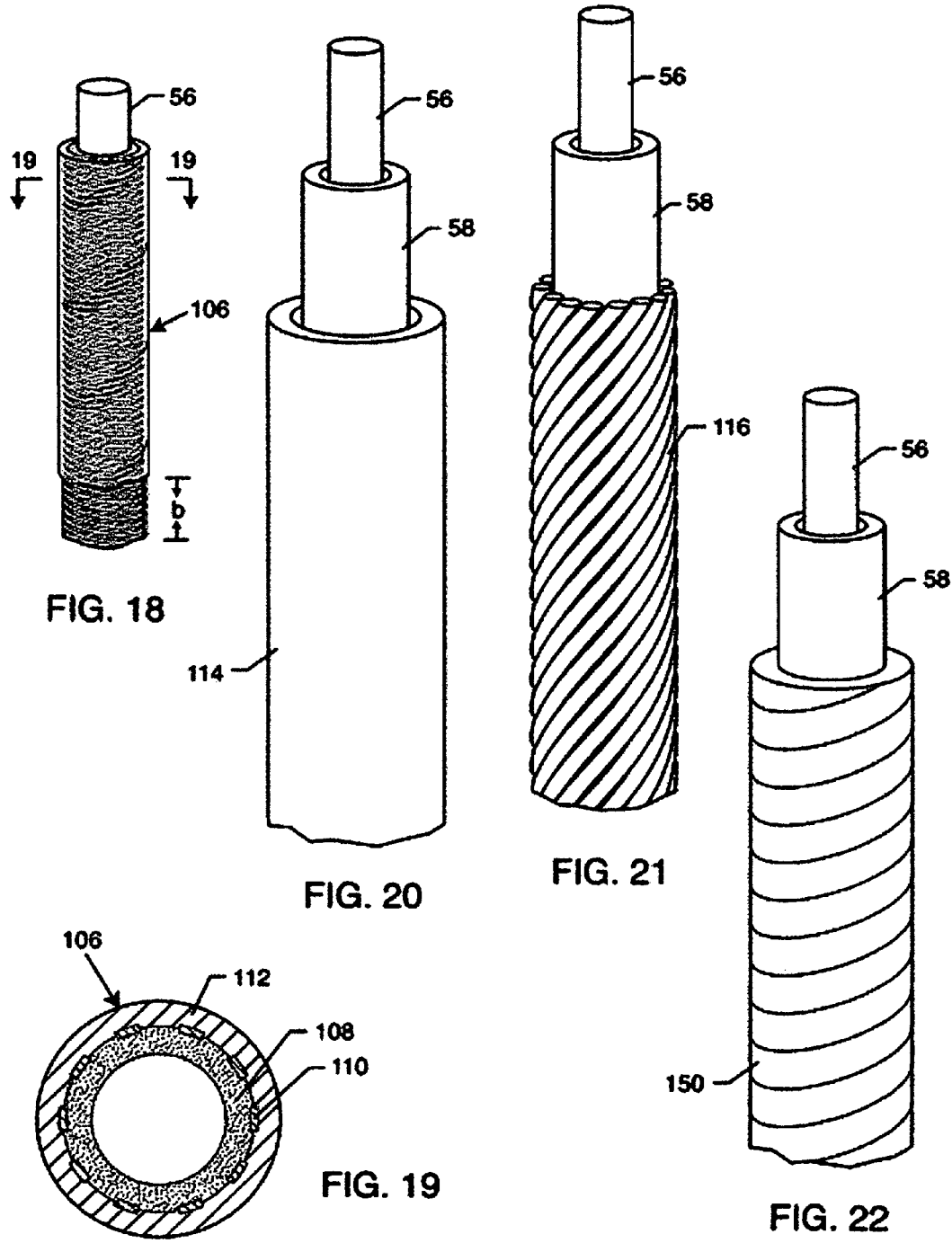

SHIELDED RF DISTANCE TELEMETRY PIN WIRING FOR ACTIVE IMPLANTABLE MEDICAL DEVICES

RELATED APPLICATIONS

This application claims priority to Provisional Application Nos. 60/594,236, filed Mar. 22, 2005, and 60/655,853, filed Feb. 23, 2005.

BACKGROUND OF THE INVENTION

Feedthrough capacitor electromagnetic interference (EMI) filters are well known in the art for decoupling and shielding of signals that are picked up by lead wires implanted in human body tissue. For example, in cardiac pacemaker applications, the wires that lead from the pacemaker to the heart often act as antennas and pick up stray electromagnetic interference from sources such as cell phones, RF identification systems, cell phone boosters, cell phone jammers, microwave ovens, and other emitters that are typically found in the patient environment. Another such powerful emitter is the RF field produced during magnetic resonance imaging (MRI). These signals often propagate into a pin and are then coupled into the interior of the active implantable medical device.

Common preferred practice in accordance with U.S. Pat. No. 5,333,095 and others is to mount a feedthrough filtered capacitor at the point of ingress and egress of the lead wires into an active implantable medical device (AIMD). Exemplary prior art EMI filters are shown and described in U.S. Pat. Nos. 5,333,095; 5,751,539; 5,896,267; 5,905,627; 5,959,829; 5,973,906; 5,978,204; 6,008,980; 6,275,369; 6,529,103; 6,643,903; 6,765,779; 6,765,780; 4,424,551; and 4,148,003, the contents of which are incorporated herein.

For high frequency EMI, such as that produced in the 450 MHz to 3000 MHz frequency range, it is very important that all of the leads that enter into and egress the AIMD be filtered. This is because once EMI enters into the housing of the AIMD, on even one lead, it can cross-couple or re-radiate to EMI sensitive adjacent circuits inside the pacemaker, implantable cardioverter defibrillator or the like. Accordingly, said EMI could find its way into a pacemaker sense circuit and create a dangerous situation, such as inhibition of the device.

In the past, telemetry was accomplished by an embedded coil that was contained in the titanium housing of the AIMD. Since the titanium shield is not magnetic, it was very easy to pass low frequency telemetry signals through close coupling subcutaneously from an external coil. This so-called external coil was held in close proximity to the AIMD allowing the physician to communicate with the AIMD. In this way, the physician could check battery status, recover patient waveforms, and also accomplish reprogramming and resetting.

However, a major market trend is that physicians and patients want to recover more and more stored data. That is, if a particular pacemaker patient is engaging in a sport activity and feels discomfort or what appears to be arrhythmias, it is desirable that the patient be able to return to the physician's office, even a week or two later, and recover the ECG waveforms from that time period. Accordingly, there is a need for more bandwidth and more stored data within the AIMD. Recent advancements in microchips allow for the storage of a great deal of data which can later be retrieved by the physician.

Another trend is that it is often inconvenient to close couple to an AIMD inside the patient. Putting a telemetry wand (head) immediately over the patient's chest and moving it around until one gets good communication with the AIMD or pacemaker is often problematic. Also, in a hospital setting it would be highly desirable to simply have a telemetry device anywhere in the patient's room that could continuously monitor and/or communicate with the pacemaker. Accordingly, there is a trend towards higher frequency (HF) distance telemetry.

In order to accomplish distance telemetry, the telemetry signals have to be at a higher frequency. In the past, the embedded coils operated in the kilohertz region with most of these between 50 and 140 kHz. For distance telemetry, there is typically an RF pin which egresses the hermetic terminal of the AIMD and sits in the device header block on the body fluid side of the AIMD housing. The device header block is typically a molded plastic or similar material. This RF pin is not connected through lead wires to body tissue. It sits in place and acts as a simple short stub antenna. The U.S. Federal Communications Commission has allocated a frequency range for such purposes called the MICCS frequency range, which is in the 400 to 405 MHz range. There are also higher frequency ranges in use around 800 to 900 MHz (or even up to 3 GHz). Advantages of such high frequencies are their relatively short wave length and efficient coupling to such a short antenna. This eliminates the need for a bulky embedded coil which was previously used inside AIMDs or in some cases it was so large that it had to be implanted external to the AIMD.

Another advantage of distance telemetry is that the band width and therefore the communication speed is much greater. That is, the physician can retrieve a great deal more data and at a faster rate than in the previous kilohertz frequency range telemetry transmissions. Accordingly, patient ECGs and other information can be readily displayed. In addition, since the higher frequency energy couples efficiently with the short RF pin antenna, it is no longer necessary to have an external telemetry head coil that is placed in close proximity to the patient's chest. That is, from a considerable distance, for example across the room, the physician can use a high frequency external programmer or an external reader and communicate with the implanted medical device.

All of this presents a problem, however, for EMI shielding within the AIMD. On the one hand, it is not possible to attach any of the prior art EMI filtered feedthrough capacitor(s) to this RF pin. The reason for this is that the broadband feedthrough capacitor filter is so efficient that it would remove the high frequency carrier along with the modulation of the telemetry signals. On the other hand, a significant problem arises when there is an unfiltered pin that ingresses and egresses the implantable medical device. It has been demonstrated through both coupling theory and laboratory testing that having an unfiltered pin enter the implantable medical device in close proximity to filtered pins can be problematic. That is, cross coupling can occur either through distributed capacitance, mutual inductive coupling or antenna propagation (re-radiation) between the unfiltered RF pin and the adjacent filtered lead wires (or directly to other circuits), such as those that may go to pacemaker sense circuits. Accordingly, having an unfiltered pin pass close to the filtered pins into the AIMD can significantly degrade the overall attenuation and shielding to electromagnetic interference.

FIG. 1 is an isometric drawing of a prior art active implantable medical device (AIMD) 30 such as a cardiac pacemaker. Referring to FIG. 1, one can see that there is a conventional titanium housing 32 which encloses and hermetically seals the electronics of the AIMD 30. There is also a header block assembly 34 into which lead wires 36 in accordance with ISO standards IS1, DF1 or the like are included. Also shown is an example of how the physician can plug in a mating plug 38 and cardiac lead 39 into the lead wire 36 assembly. In typical prior art applications, this would allow the physician to plug in lead wires 39 that are designed, for example, to be placed into the chambers of the heart 40. Referring back to FIG. 1, one can see an RF telemetry pin 42 which extends through the header or terminal 44 of the AIMD 30. One will notice that the RF telemetry pin 42 is not connected to any of the lead wires 36 within the header block 34 itself. The RF telemetry pin 42 forms a short stub antenna which is designed to communicate with an external transmitter used by a physician or other hospital personnel. The length of the RF telemetry pin 42 is important in that it should match a fraction of the wave length of the transmitted signal. According to the prior art, RF telemetry pin 42 could be associated with an overall hermetic seal or it can be installed with its own discrete hermetic seal.

FIG. 2 is a sectional view taken generally along line of 2-2 of FIG. 1. FIG. 2 shows the RF telemetry pin 42 in relation to the cardiac pacing and sensing lead wires 36. Also shown is a prior art feedthrough capacitor 46 which has been generally described by U.S. Pat. Nos. 4,424,551; 5,333,095; 5,905,627; 6,765,779 and the like. The AIMD 30 may be exposed to electromagnetic interference (EMI). These EMI signals impinge upon the housing 32. When the housing is metallic such as titanium the EMI is reflected off of or absorbed by the shielding material (shown as 48a). EMI may also couple into the lead wires 36 of the AIMD 30 that are designed to connect to body tissue (shown as 48b). However, the presence of feedthrough capacitor 46 generally decouples or shorts such EMI to the housing 32 of the AIMD 30 where it is dissipated as harmless heat energy. This prevents such EMI from entering into the inside of the AIMD 30 via the lead wires 36 and disrupting sensitive electronics. However, EMI may also couple to the RF telemetry pin 42. In other words, in addition to coupling to desirable RF telemetry signals, the RF telemetry pin 42 also picks up stray EMI signals (shown as 48c). These EMI signals are readily couple to the inside of the AIMD 30 (shown as 48d) where they can re-radiate to sensitive electronics such as the pacemaker sense circuits. A concern is that such EMI could be sensed as a normal cardiac rhythm which could cause, for example, a pacemaker to inhibit.

Accordingly, there is a need for an unfiltered but shielded RF telemetry pin, which is designed in such a way that it does not cross-couple, re-radiate or otherwise degrade the attenuation of adjacent filtered circuits. Additionally, there is a need for a methodology of shielding said RF pin wiring against such EMI so that the EMI cannot re-radiate or couple to sensitive AIMD electronics that are inside the AIMD housing. The present invention fulfills these needs and provides other related advantages.

SUMMARY OF THE INVENTION

This invention relates to electromagnetic interference (EMI) filter terminal assemblies for active implantable medical devices (AIMDs). In particular, the invention provides for an EMI filter terminal assembly for an AIMD comprising a conductive ground plane (which may be in the form of a ferrule) and a feedthrough capacitor having first and second sets of electrode plates, wherein the second set of electrode plates are conductively coupled to the ground plane. A lead wire extends into the capacitor in conductive relation with the first set of electrode plates. In addition, a radio frequency (RF) telemetry pin extends through the ferrule in non-conductive relation and includes a conductive shield extending over a portion of the RF telemetry pin in non-conductive relation with the telemetry pin, wherein the conductive shield is conductively connected to a ground associated with the AIMD. The assembly may also include an insulation tube between the RF telemetry pin and the conductive shield covering a portion of the RF telemetry pin at least coextensive with the conductive shield. The insulation tube may be comprised of Kovar or a polyimide such as plastic, Teflon, or silicone, or the like, or it may comprise a conductive heat shrink tubing, wherein the exterior surface forms at least a portion of the conductive shield. The conductive shield may be comprised of any suitable conductive material such as gold, copper, nickel or another material providing suitable electro-magnetic shielding and may be in the form of a coating, a plating, a solid metal tube, a wound wire tube, a braided wire tube or wrapped foil tube. Where the conductive shield is a wound wire tube or a braided wire tube it may be comprised of 304 V stainless steel.

The assembly may further comprise a circuit board or substrate having a wire bond pad that is conductively coupled to the RF telemetry pin. The circuit board or substrate may further comprise a second wire bond pad that is conductively coupled to the conductive shield which is at AIMD housing ground potential. The conductive coupling of the RF telemetry pin and/or the conductive shield to the respective wire bond pads may be accomplished by thermal bonding, ultrasonic bonding, soldering, brazing, welding or a conductive adhesive.

The feedthrough capacitor may include a metal coating or metallization covering at least a portion of the outer surface, wherein the metal coating or metallization is conductively coupled to the second set of electrode plates and to the ground plane. This metal coating or metallization may also be conductively coupled to the conductive shield by means of a solder, a braze, or a thermal setting conductive adhesive. Alternatively, a conductive metal frame may cover a portion of the outer surface of the feedthrough capacitor and be conductively coupled to the ground plane and the conductive shield.

The assembly may further comprise a terminal insulator mechanically coupled to the ground plane through which the RF telemetry pin passes in non-conductive relation. The terminal insulator may include a counterbore surrounding the RF telemetry pin as it passes through the terminal insulator to limit the distributed capacitance between the AIMD housing and the RF telemetry pin. Alternatively, the RF telemetry pin may include a notch or swadge around its perimeter as it passes through the terminal insulator.

In addition to the insulation tube and the conductive shield, the RF telemetry pin may further include an exterior insulation layer. The exterior insulation layer may comprise a polyimide tubing. Where the conductive shield is conductively coupled to the second set of electrode plates, a portion of the exterior insulation layer may be removed at the point of coupling.

In an alternative embodiment, the EMI filter terminal assembly comprises a conductive ground plane associated with a housing for the AIMD. A first terminal insulator is mechanically coupled to the conductive ground plane and a lead wire passes therethrough in non-conductive relation. A second terminal insulator is mechanically coupled to the conductive ground plane. The RF telemetry pin extends through this second terminal insulator in non-conductive relation and the conductive shield extending over a portion of the RF telemetry pin is conductively connected to the conductive ground plane. The conductive ground plane may comprise one or more conductive ferrules.

The assembly of the present invention may be used with various AIMDs including a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, or a prosthetic device.

These and other aspects of the invention will be apparent to one skilled in the art in light of the following detailed description of the preferred embodiments.

BRIEF DESCRIPTION OF THE DRAWINGS

The following drawings illustrate the invention. In such drawings:

FIG. 18 is a perspective view of reinforced polyimide tubing which can be used for the shielded telemetry pin;

FIG. 19 is a sectional view taken generally along the line 19-19 of FIG. 18;

FIG. 20 is a perspective view similar to FIG. 18, illustrating an alternative embodiment where commercially available insulated tubing is slipped over the RF telemetry lead wire, which assembly is then placed within a soft copper tube;

FIG. 21 is a perspective view similar to FIG. 20, wherein the solid metal tube of FIG. 20 has been replaced by wound wire strands;

FIG. 22 is a perspective view similar to FIG. 20, wherein the solid metal tube of FIG. 20 has been replaced by wrapped foil.

DETAILED DESCRIPTION OF THE PREFERRED EMBODIMENTS

The present invention provides a variety of shields that surround a radio frequency (RF) telemetry pin lead wire on the inside of an active implantable medical device (AIMD). These shields act to prevent re-radiation of unwanted stray signals including telemetry signals themselves to adjacent sensitive circuits such as the sense circuits of an implantable cardiac pacemaker or other implantable device.

It is also very important that an RF telemetry circuit be efficient and well impedance matched. This is because significant attenuation could cause degradation of the distance telemetry signal. One of the major features of distance telemetry is that close coupling is not required. Accordingly, any degradation of the signal as it enters or exits the AIMD is undesirable. Accordingly, the shielding systems used to surround an RF telemetry pin lead wire on the inside of the AIMD device should be highly efficient in impedance match. This is accomplished through selection of proper insulating materials, their dielectric constants and other electrical properties, and the proper outside diameter (OD) to inside diameter (ID) ratios to the shield.

Figure 1:
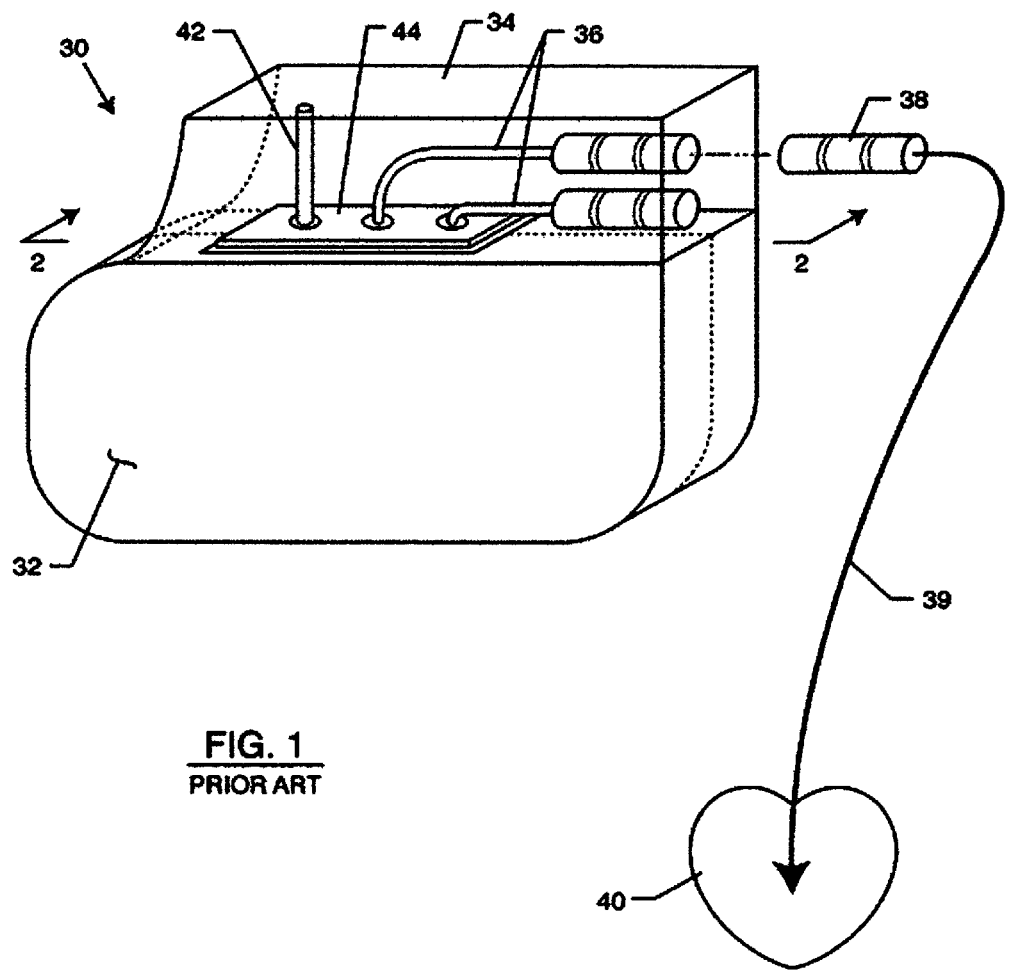
FIG. 1 is an isometric drawing of a prior art active implantable medical device such as a cardiac pacemaker.
Figure 2:
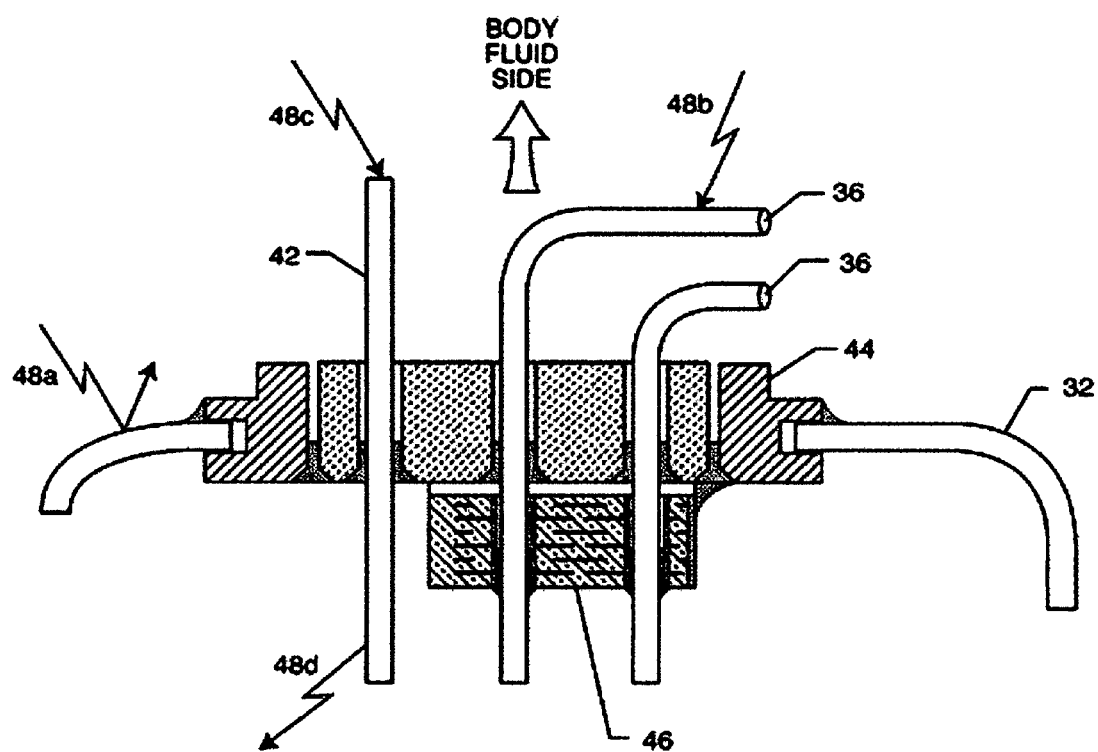
FIG. 2 is a cross-sectional view taken generally along line 2-2 of FIG. 1.
Figure 3:
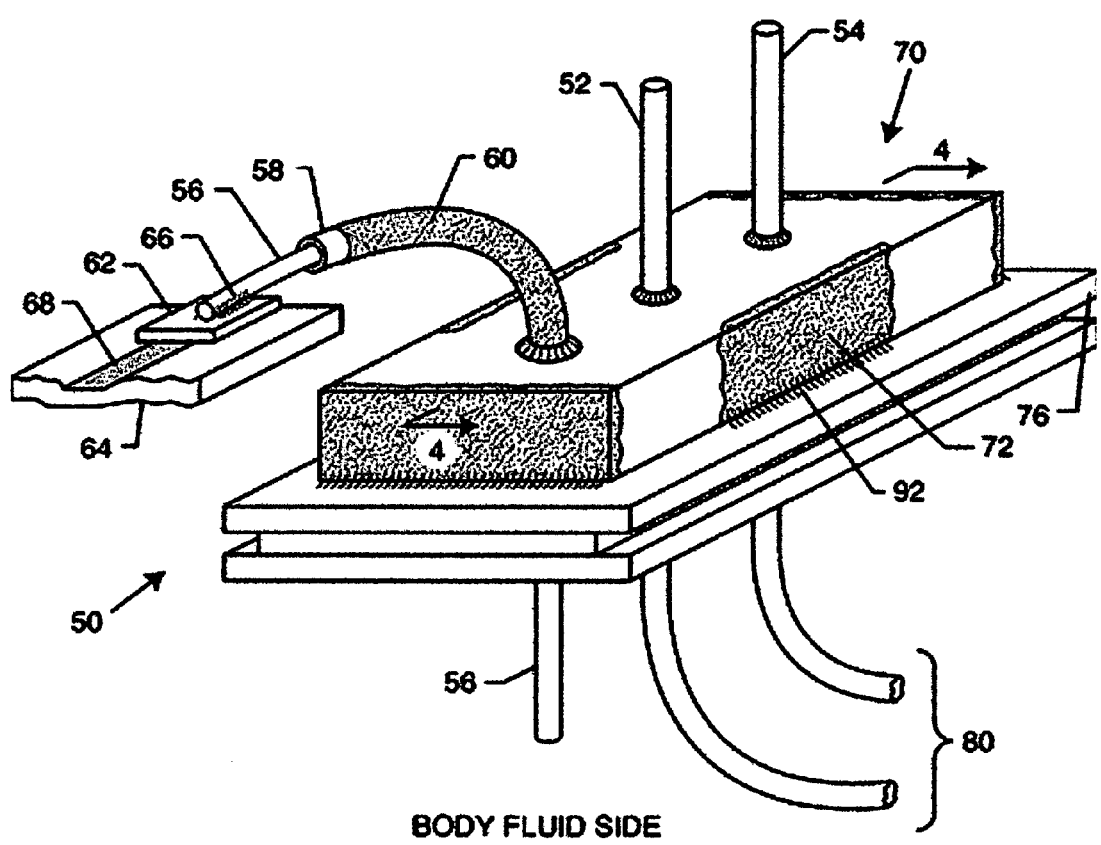
FIG. 3 is a perspective view of a bipolar EMI filtered terminal including a shielded RF telemetry pin.

FIG. 3 is a drawing of a bipolar electromagnetic interference (EMI) filtered terminal 50 embodying the present invention. Bipolar pacemakers are well known in the art. In this example, this is a cardiac pacemaker with a bipolar lead that is routed from the pacemaker to the right ventricle. The bipolar lead system typically has a Tip and Ring electrode at the distal end. For example, lead wire 52 could be routed to the distal Tip and lead wire 54 could be routed to the distal Ring. Pacing pulses are then applied to lead wires 52 and 54. In addition, sensing of cardiac signals can also be accomplished by these lead wires. Also shown is pin 56, which on the body fluid side, is an RF telemetry pin antenna. RF distance telemetry pins are known in the art as previously described.

A novel feature of the invention is shown in the insulation tube 58 and surrounding conductive shield 60. The insulation tube 58 can be any one of a number of insulators including any of a wide range of plastics, Teflons, silicones or the like. In a preferred embodiment, it would be a thin walled non-conductive polyimide or Kovar tubing. This is preferable because of its ability to withstand high temperatures and its flexible nature. This allows the manufacturer of the cardiac pacemaker to route the shielded tubing which protects the RF telemetry lead wire to any desired location within the housing of the active implantable medical device. A conductive shield 60 is placed over the insulation tube 58. In a preferred embodiment, conductive shield 60 is a thin layer of gold plating applied directly to the insulation tube 58 itself. However, conductive shield 60 may be a braided, wrapped, or solid metal tube, any of which are commonly used in prior art RF cables. Solid copper tubing or a variety of other conductive materials can be used. It will be obvious to those skilled in the art that a wide variety of materials are available for the insulation tube 58 and the conductive shield 60. For example, conductive heat shrink tubing could be used which combines the properties and features of the insulation tube 58 and the conductive shield 60. Moreover, the conductive shield 60 could be formed utilizing cathodic arc, physical vapor deposition, ion beam implantation, laser induced deposition, or electroplating processes. It is not necessary to have 100% coverage of the insulation tube 58 by the conductive shield 60 to have good RF field containment and prevent coupling to AIMD circuitry or to adjacent pins 52 and/or 54. The conductive shield 60 could even be of nickel ferro-nano particles or other suitable magnetic shielding material protecting against MRI signals as well.

Referring once again to FIG. 3, one can see that the RF telemetry pin antenna 56 can now be conveniently routed to a wire bond pad 62 on a circuit board or substrate 64 on which other electronic components are mounted. The exposed RF telemetry pin antenna 56 is shown attached to wire bond pad 62 through wire bonding 66 or ultrasonic bonding, soldering or the like. A circuit trace 68 connects from the wire bond pad area 62 to a nearby hybrid circuit (not shown) which detects the high RF telemetry and converts it to low frequency digital pulses.

It is highly desirable that the hybrid circuit be as close to the wire bond pad 62 and the termination of the shield 60 as possible. Keeping this distance very short will minimize any RF re-radiation within the AIMD. Extremely short lead wires are inefficient couplers or re-radiators at the wave lengths contemplated for distance RF telemetry. However, if unsealed telemetry pin wiring 56 was routed long distances, then re-radiation becomes a definite possibility.

The bipolar feedthrough capacitor 70 with RF telemetry pin antenna 56, as previously described, has ground terminations 72 which connect to the ground electrode plates 74 (see FIGS. 4 and 5) in the capacitor 70. There is an electrical connection 92 between these ground terminations 72 and the ferrule 76 of the hermetic terminal 50 of the implantable medical device. This connection is typically made to a gold bond pad 78 (FIG. 4) as described in U.S. Pat. No. 6,765,779.

In the case of an internally grounded feedthrough capacitor such as that described in U.S. Pat. Nos. 5,905,627 and 6,529,103, the capacitor's ground electrode plates are grounded through a pin which is grounded to the ferrule and/or case of the AIMD. The ground electrode plates of the internally grounded capacitor can also in turn be used to ground the novel shield of the RF pin wiring as described in the present invention.

Figure 8:
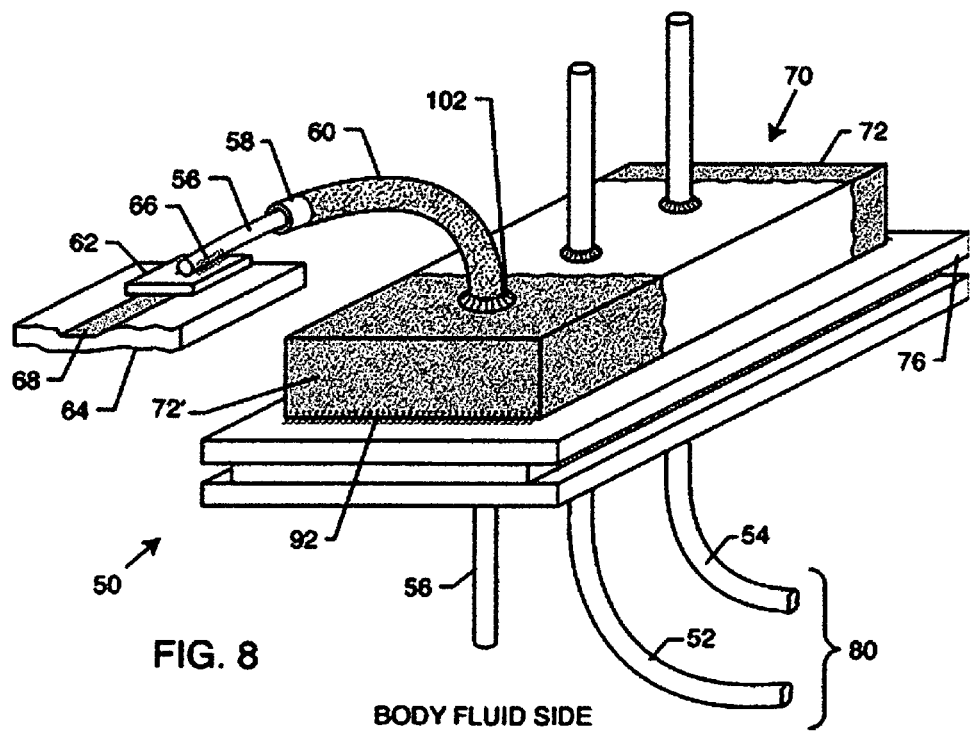
FIG. 8 is a perspective view similar to FIG. 3, illustrating an alternative method of grounding the RF telemetry lead wire shield to the feedthrough capacitor.
Figure 9:
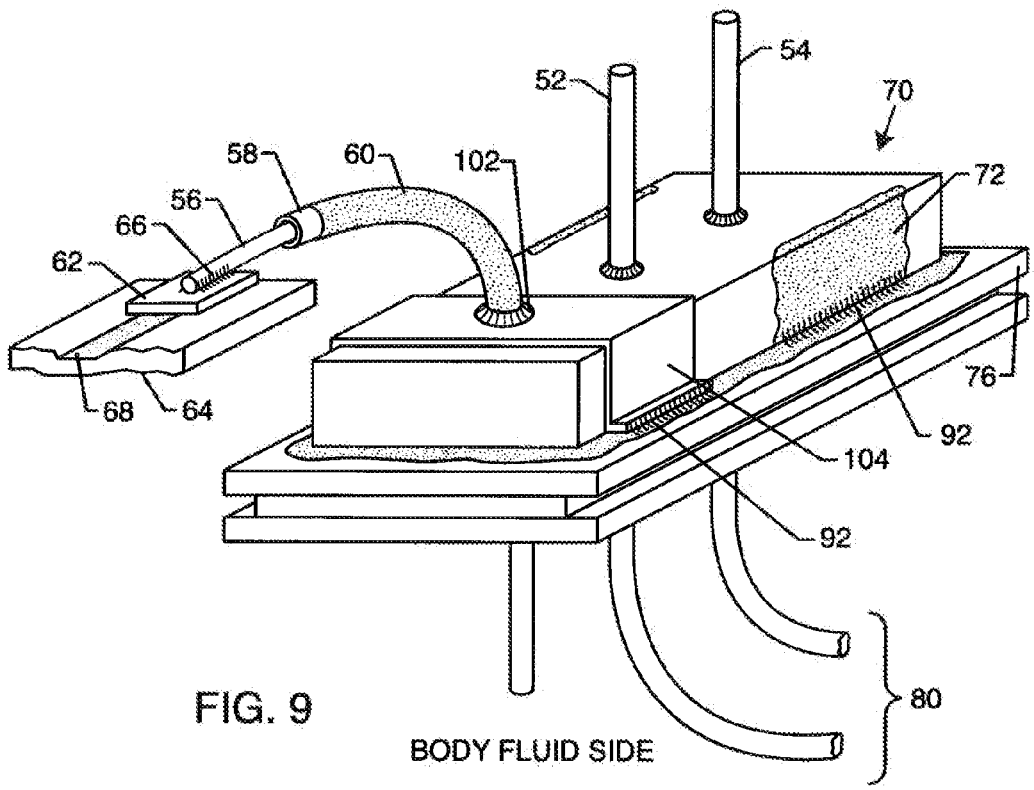
FIG. 9 is a perspective view similar to FIG. 3, illustrating yet another alternative embodiment of providing an RF ground to the RF pin shield.
Figure 10:
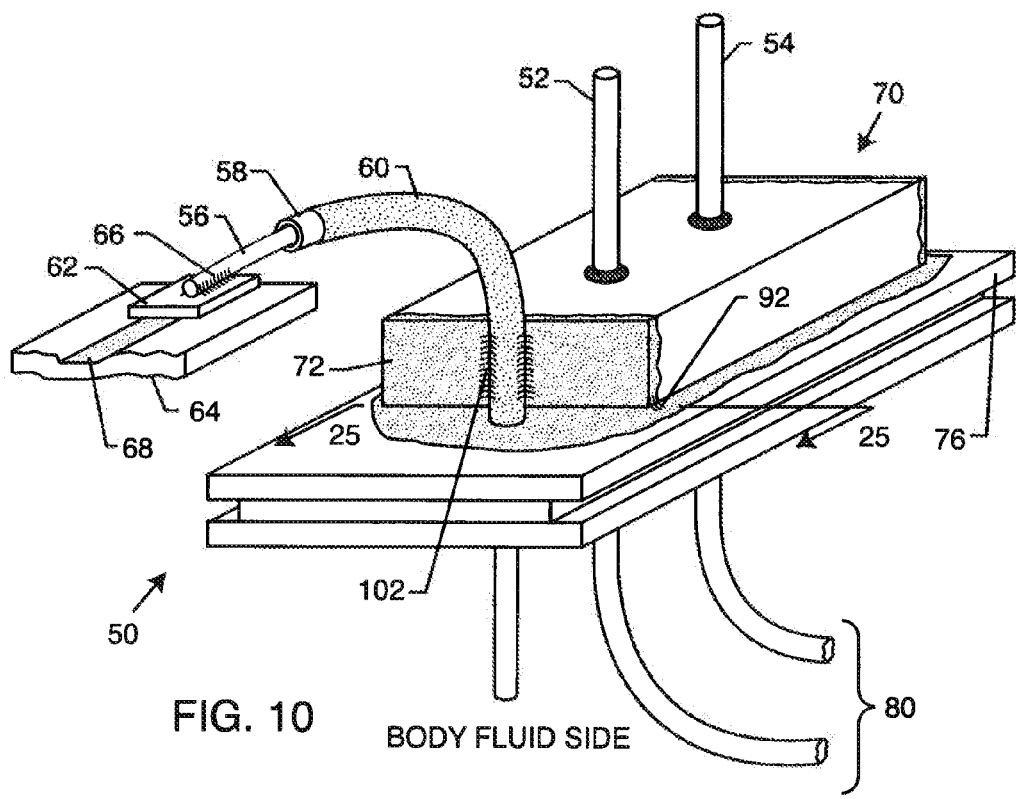
FIG. 10 is a perspective view similar to FIG. 3, illustrating yet another method of providing an RF ground to the shield of the RF pin.

Referring to FIGS. 8, 9 and 10 showing the body fluid side of the hermetic terminal 50, the RF telemetry pin antenna 56 terminates within a header block (not shown) and does not make direct contact with body tissue. However, cardiac pacing and sensing leads 52 and 54 are routed through to the venous system 80, typically through the subclevian vein down through the aortic arch and into the right ventricle. Accordingly, this is convenient for pacing and sensing electrical signals. Other applications in addition to cardiac pacemakers and sensing systems that will be obvious to those skilled in the art are a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, or a prosthetic device and any other application where lead wires are implanted into body tissue. Any and all of these devices can feature an RF telemetry pin antenna 56 for convenient device programming or for downloading of stored data from the AIMD.

Figure 4:
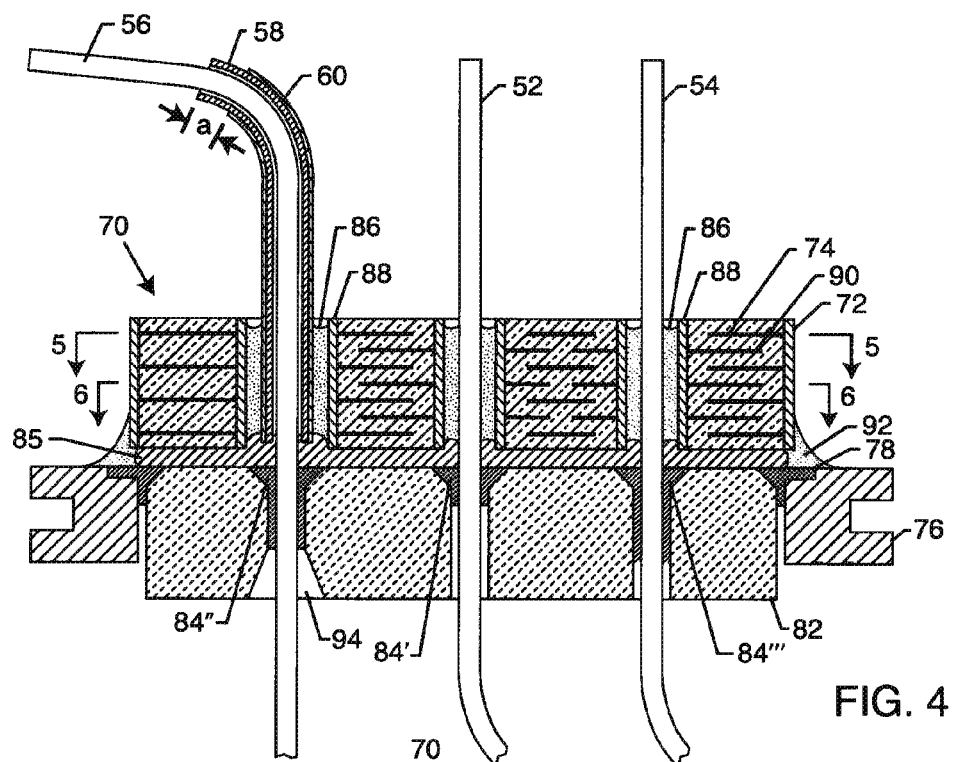
FIG. 4 is an enlarged sectional view taken generally along the line 4-4 of FIG. 3.

FIG. 4 is a cross-section of the bipolar filtered hermetic terminal 50 previously described in FIG. 3. Bipolar pins 52 and 54 are typical of prior art EMI filters. That is, they pass through the alumina terminal insulator 82 in non-conductive relation. There is a gold braze 84 which forms a hermetic seal between the alumina insulator 82 and the corresponding lead wire 52, 54 or pin 56. A non-conductive washer 85 or similar material can be disposed between the capacitor 70 and the alumina insulator 82. The sensor/pacing lead wires 52, 54 then pass through the apertures of the feedthrough capacitor 70 where they are connected through electrical connection material 86 to the capacitor inside diameter metallization 88 which connects to the capacitor's active electrode plates 90. In a corresponding fashion, the capacitor's outside diameter metallization 72 is connected to the capacitor's ground electrode plates 74. Electrical connection material 92 makes connection between the capacitor outside diameter metallization 72 and the metallic ferrule 76 of the implantable medical device. As previously described in U.S. Pat. No. 6,765,779, it is important that electrical connection material 92 make contact to gold braze area 78 in order to provide a reliable oxide free electrical connection.

Referring once again to FIG. 4, the RF telemetry pin antenna 56 is shown as previously described in FIG. 3. As shown in cross-section, the insulation tube 58 extends slightly past the surrounding conductive shield 60. In the preferred embodiment, conductive shield 60 would be soft gold plating. In a low voltage device such as a cardiac pacemaker or neurostimulator, it is not necessary that insulation tube 58 protrude very far past the conductive shield 60—shown as distance "a". However, in a high voltage device, such as an implanted cardioverter defibrillator, it is preferable to have a significant separation distance "a" in order to increase the high voltage flashover distance between the conductive shield 60 and the RF telemetry pin antenna 56. The separation distance "a" should be of sufficient length to prevent such high voltage flashover and the required distance will be apparent to those having ordinary skill in the art. Referring again to RF telemetry pin antenna 56, where it enters the inside diameter of the feedthrough capacitor 70, an electrical connection material 86 is used to connect the conductive shield 60 to the capacitor ground electrode plates 74 through the inside diameter metallization 88. This is a very novel and efficient way of connecting the conductive shield 60 to a ground point. That is, in the preferred embodiment, the ground electrode plates 74 of the capacitor 70 will also be used to ground the conductive shield 60 on the RF telemetry pin antenna wire 56.

The distance of gold braze penetration, otherwise known as pull through, in 84' compared to 84''' is a variable and depends upon complex wetting and capillary characteristics. One cannot rely on a short amount of gold braze penetration as shown in 84'. An additional complication is that the degree of gold braze penetration can vary from pin to pin as shown for 84''' which has excessive penetration. It is desirable to limit the amount of capacitance between the shielded RF telemetry pin antenna 56 and the ferrule 76. If there is too much distributed capacitance or stray capacitance between these two points, this will leak off (attenuate) the desirable high frequency telemetry signal. Also, in order to be able to keep the characteristic impedance of the line consistent, it is important that there is not too much variability in this distributed capacitance in the hermetic terminal 50 itself. One can see in comparing 84' to that of the gold braze shown in 84''', that there is considerable variability in the amount of gold braze penetration. The amount of distributed capacitance between the pin 56 and the ferrule 76 will be higher for the gold braze penetration shown in 84''' than it would be for 84'. Accordingly, it is desirable to maintain not only minimal penetration of the gold braze, but also consistent penetration of the gold braze. A novel aspect of the present invention is the counterbore 94 shown adjacent to 84". This counterbore 94 will limit the amount of gold braze penetration by interrupting the capillary action and other factors. This is a practical way of achieving consistent penetration of the gold braze since during manufacture of the hermetic terminal 50 and subsequent gold brazing, the amount of gold braze penetration is otherwise variable. Such things as capillary action, surface tension, fixture alignment and dimensional variability all affect the amount of gold braze penetration. Accordingly, the novel counterbore 94 as illustrated in FIG. 4 guarantees that the amount of gold braze penetration be both limited and consistent. It would not matter if the gold braze actually came down and wetted the inside of the counterbore 94 since that area is not immediately adjacent to pin 56 (the air gap prevents the buildup of stray capacitance). Accordingly, a novel feature of the present invention is the control of said gold braze penetration with the counterbore 94 as shown. It should be noted that the gold braze 84', 84" and 84''' are illustrative only. The aforementioned discussions apply lead wires 52, 54. Additional capacitance to ground, for example in lead wires 52, 54, would add additional EMI filtering which would be desirable for normal pacemaker sensing and pacing circuitry. Accordingly, the counterbore 94 is particularly desirable and applicable to the RF telemetry pin antenna 56. It will be obvious to those skilled in the art that other geometric structures can also be used to limit and control the amount of gold braze penetration.

Figure 5:
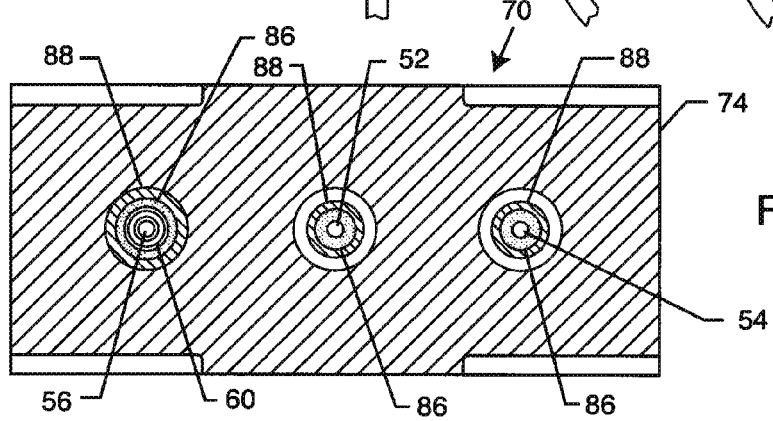
FIG. 5 is a sectional view taken generally along the line 5-5 of FIG. 4, illustrating the configuration of ground electrode plates within the feedthrough filter capacitor.
Figure 6:
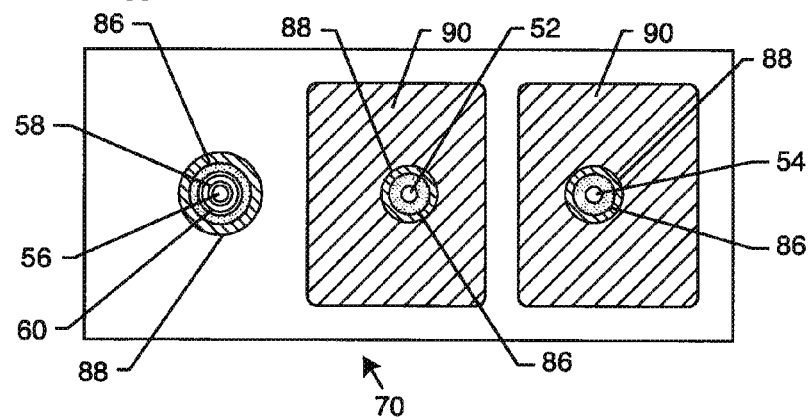
FIG. 6 is a sectional view taken generally along the line 6-6 of FIG. 4, illustrating the configuration of active electrode plates within the capacitor.

FIGS. 5 and 6 show both the ground and active electrode plates 74 and 90 of the bipolar feedthrough capacitor of FIGS. 3 and 4. The ground electrode plates are shown in FIG. 5 and are labeled 74. As is well known in the art, there can be one, two, or even greater than one hundred such ground electrode plates. In a corresponding manner, the active electrode plates 90 are shown in FIG. 6. The active electrode plates 90 are interleaved between said ground electrode plates 74. It is the overlap of the active electrode plates 90 and the ground electrode plates 74 that forms the EMI filter capacitor 70. Referring once again to FIG. 5, the conductive shield 60 of the RF telemetry pin antenna 56 is electrically connected through conductive material 86 to the inside diameter metallization 88 of the plurality of ground electrode plates 74. Referring to FIG. 6, one can see that there are no active electrode plates 90 associated with RF telemetry pin antenna 56.

In the following descriptions of the FIGURES, functionally equivalent components common to the various embodiments are referred to by the same reference number.

Figure 7:
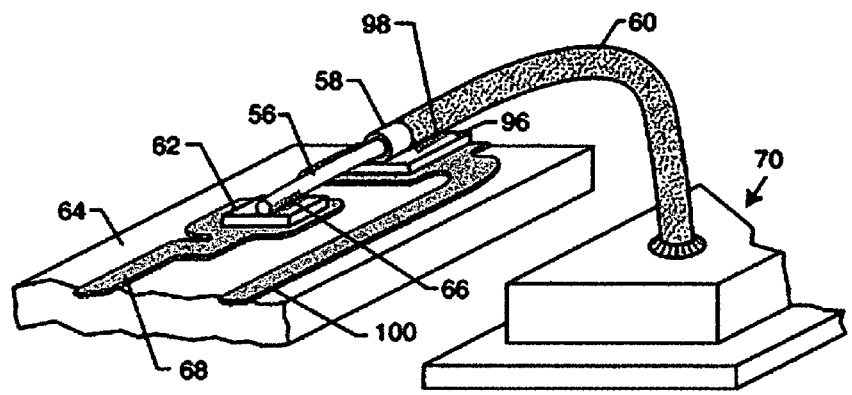
FIG. 7 is a fragmented perspective view similar to that shown in FIG. 3, illustrating an alternative method of making connection to an electrical component or a circuit substrate located inside the housing of an AIMD.

FIG. 7 illustrates an alternative method of making connection to an electrical component, a circuit board, or a circuit substrate located inside the housing of the implantable medical device. Here, the RF telemetry pin antenna 56 has been attached to a circuit attachment point such as a wire bond pad 62. Connection 66 is typically comprised of ultrasonic or thermal wire bonding, solder, conductive adhesives or the like. FIG. 7, however, differs from FIG. 3 in that the conductive shield 60 that surrounds RF telemetry pin antenna 56 is connected to a second wire bond pad 96. This allows for convenient RF grounding of the circuit board 64 and also terminates the conductive shield 60 in two locations. That is, the conductive shield 60 is terminated to the ground electrode plates 74 of the feedthrough capacitor 70 and also to the circuit board connection point 96. This improves the RF shielding efficiency of the conductive shield 60. Connection 98 is very similar to connection 66 and can be accomplished by solder, thermal setting conductive adhesives and the like. It will generally not be possible to do ultrasonic or thermal sonic wire bonding for conductive shield 60 unless it is of pure gold. It is quite common in implantable medical devices such as cardiac pacemakers to require an RF ground to the circuit board 64 or substrate. An example would be in a unipolar pacing mode where the housing or can becomes the other electrode. Another example is in certain ICD configurations where the housing or can becomes one of the shock electrodes (hot can). To this end, many device designs require the welding of a pin to the inside of the titanium housing of the medical device wherein said pin is then routed to the circuit board or substrate. Use of the conductive shield 60 of the RF telemetry pin antenna 56 for this purpose is convenient in that it eliminates the necessity for the secondary step of welding such a pin to the inside of the housing of the AIMD. Accordingly, circuit trace 100 can be used for various purposes in the circuit grounding scheme. In this regard, circuit traces 68 and 100 could be routed to a hybrid circuit or chip. It is desirable to have this as close to the wire bond pad points 62 and 96 so as to minimize re-radiation of stray EMI signals that could enter via the RF telemetry pin antenna 56.

FIG. 8 illustrates an alternative method of grounding the conductive shield 60 to the feedthrough capacitor 70. In this case, the capacitor ground metallization 72' has been extended over the entire end of the capacitor 70 to include the area where the conductive shield 60 of the RF telemetry pin antenna 56 comes to the ceramic capacitor. In this case, it is not necessary that the conductive shield 60 penetrate down into the inside diameter hole of the feedthrough capacitor 70. Instead, an electrical connection 102 is made between the conductive shield 60 and the capacitor metallization 72'. Said electrical connection 102 can be comprised of solders, brazes, thermal setting conductive adhesives and the like.

FIG. 9 represents yet another alternative embodiment of providing an RF ground to the conductive shield 60. In this case, a stamped metal frame 104 has been placed over and electrically connected to the ferrule 76 of the hermetic terminal 50. The electrical connection 92 is typically comprised of solder, braze, weld, thermal setting conductive adhesive or the like. Electrical connection 102 connects the conductive shield 60 of the RF telemetry pin antenna 56 to the conductive frame 104 for the purposes of providing an RF ground. It will be obvious to those skilled in the art that the metal frame 104 can take on many sizes and shapes.

FIG. 10 provides yet another method of terminating or providing an RF ground to said conductive shield 60 of the RF telemetry pin antenna 56. One can see that the bipolar feedthrough capacitor 70 has ground terminations 72 on both ends. In this case, the capacitor 70 has been shortened so that it butts up against the conductive shield 60 that surrounds the RF telemetry pin antenna 56. An electrical connection 102 is made that provides an RF ground attachment to the ground electrode termination 72 of the capacitor 70. This material can be solder, a conductive thermal setting material or the like. It is a desirable feature to have additional ground contact points 92 between capacitor metallization 72 and the ferrule 76 of the hermetic terminal 50. The reason for this is to provide a low impedance RF ground at multiple points. If too much inductance were to build up in the ground system then the conductive shield 60 that surrounds the RF telemetry pin antenna 56 would not be as effective.

FIGS. 11-15 illustrate further alternative embodiments of EMI filtered terminals 50 embodying the present invention. These alternate embodiments provide for different configurations of the RF telemetry pin antenna 56, the insulation tube 58, the conductive shield 60, the capacitor 70, the ground terminations 72, and the additional ground contact points 92.

Figure 11:
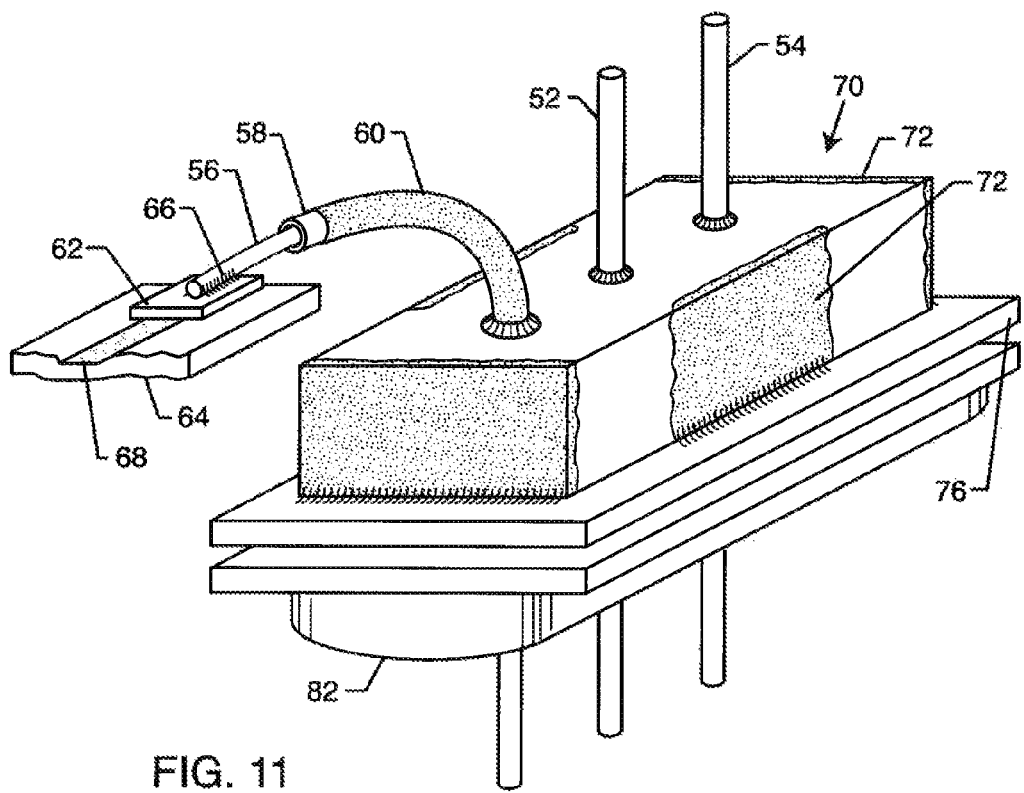
FIG. 11 is a perspective view similar to FIG. 3, illustrating an optional configuration of the EMI filter terminal and shielded telemetry pin.
Figure 12:
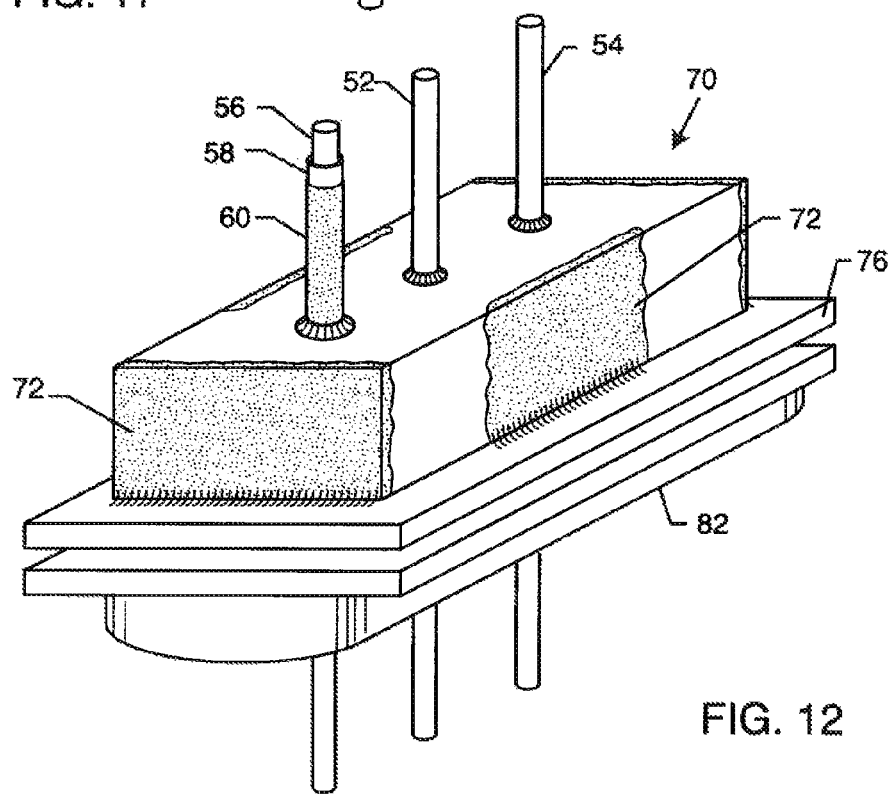
FIG. 12 is a perspective view similar to FIG. 3, illustrating an optional configuration of the EMI filter terminal and shielded telemetry pin.
Figure 13:
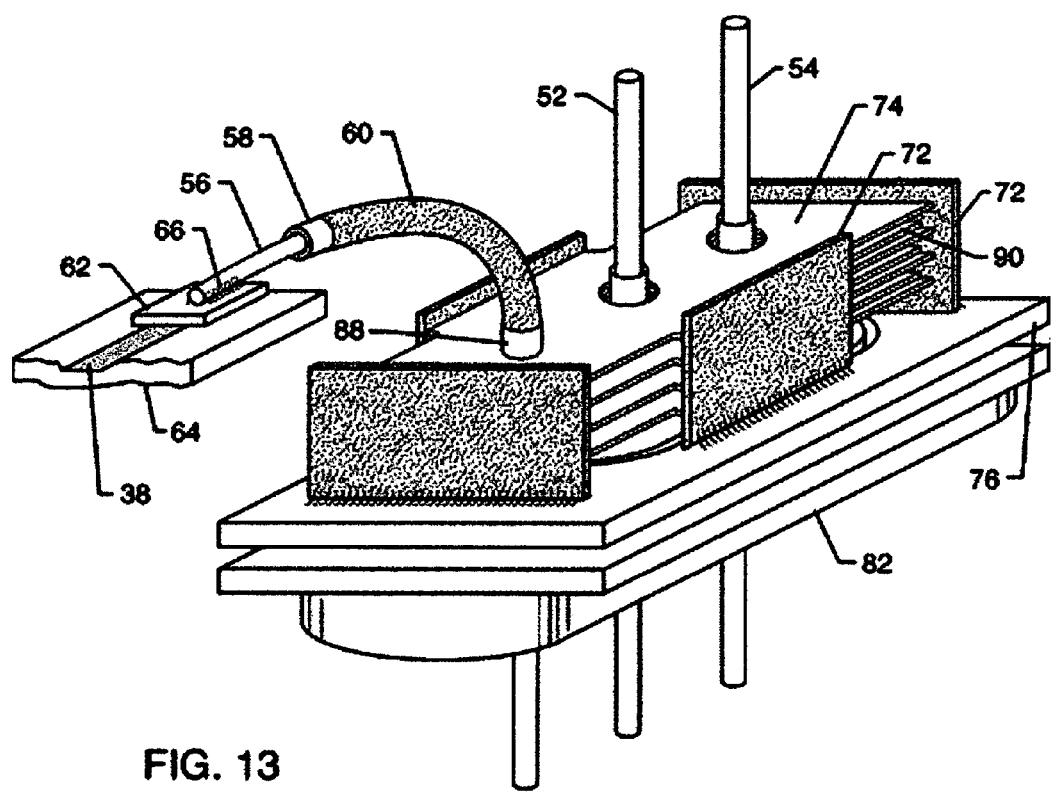
FIG. 13 is a perspective view similar to FIG. 3, illustrating an internal electrode configuration of the EMI filter terminal and shielded telemetry pin.
Figure 14:
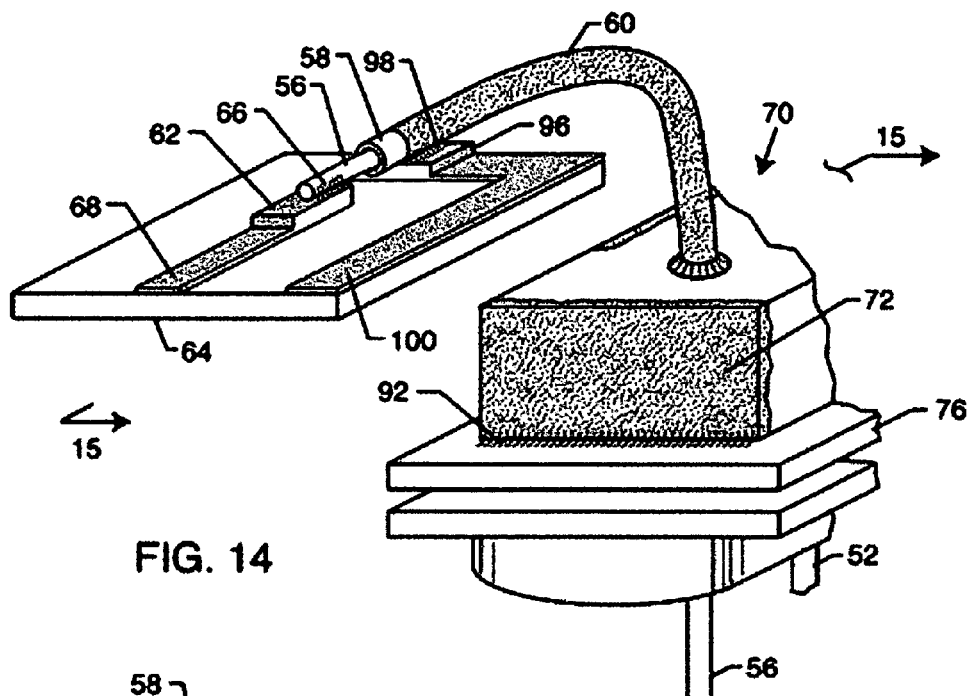
FIG. 14 is a perspective view similar to FIG. 3, illustrating yet another optional configuration of the EMI filter terminal and shielded telemetry pin.
Figure 15:
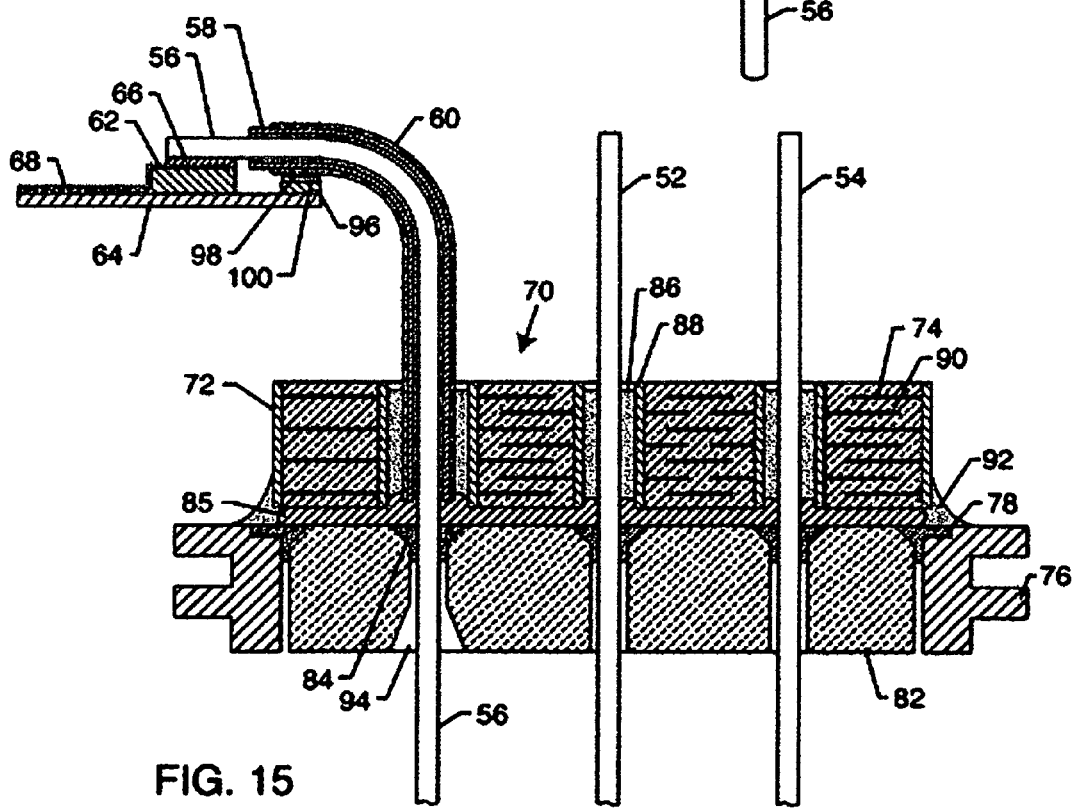
FIG. 15 is a sectional view taken generally along the line 15-15 of FIG. 14.

FIG. 13 illustrates the capacitor of FIG. 11 with all of the dielectric material removed. This allows one to see the capacitors ground electrode plates 74 in situ. As one can see, the ground connections 72 between the capacitor electrode plates 74 and the ferrule 76 is accomplished in four locations. This makes for a very low impedance ground connection. One can also see that the conductive shield 60 is terminated to the inside diameter metallization 88 providing a very low impedance RF ground.

Figure 16:
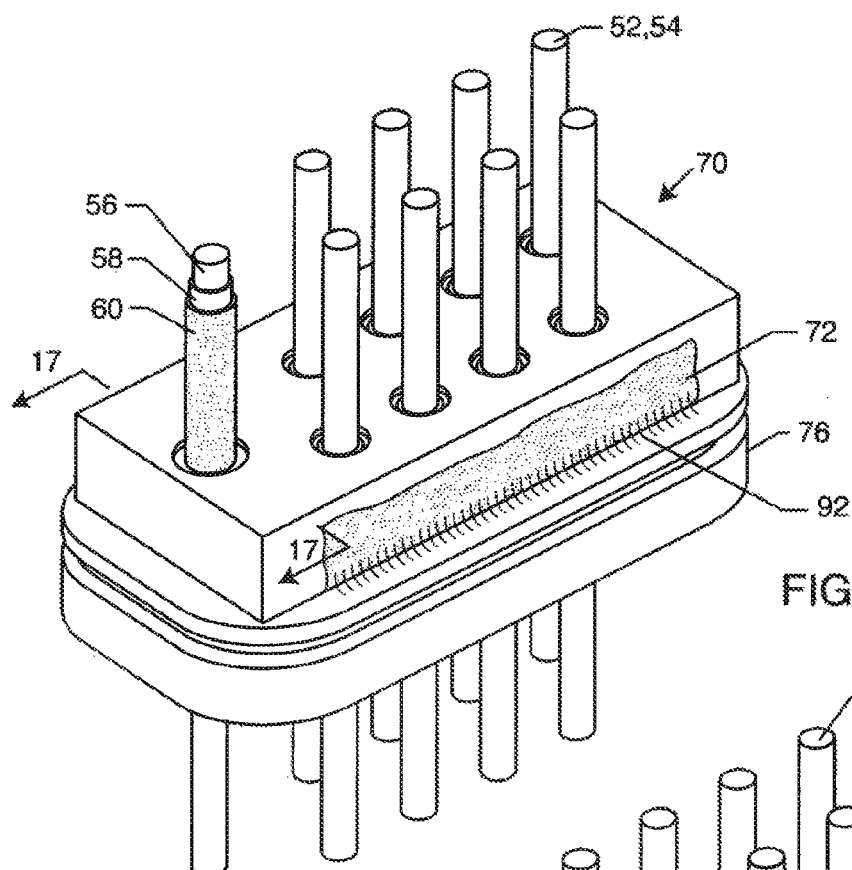
FIG. 16 is a perspective view of yet another embodiment of the invention showing a dual inline 8-pin EMI filtered terminal incorporating a ninth shielded telemetry pin in accordance with the present invention.

FIG. 16 is another embodiment showing a dual inline 8-pin EMI filtered hermetic terminal 50. The 8 pins are filtered in accordance with prior art techniques. The 9$^{th}$ pin, which corresponds to an RF telemetry pin antenna 56, incorporates the insulation tube 58 and conductive shield 60 of the present invention.

Figure 17:
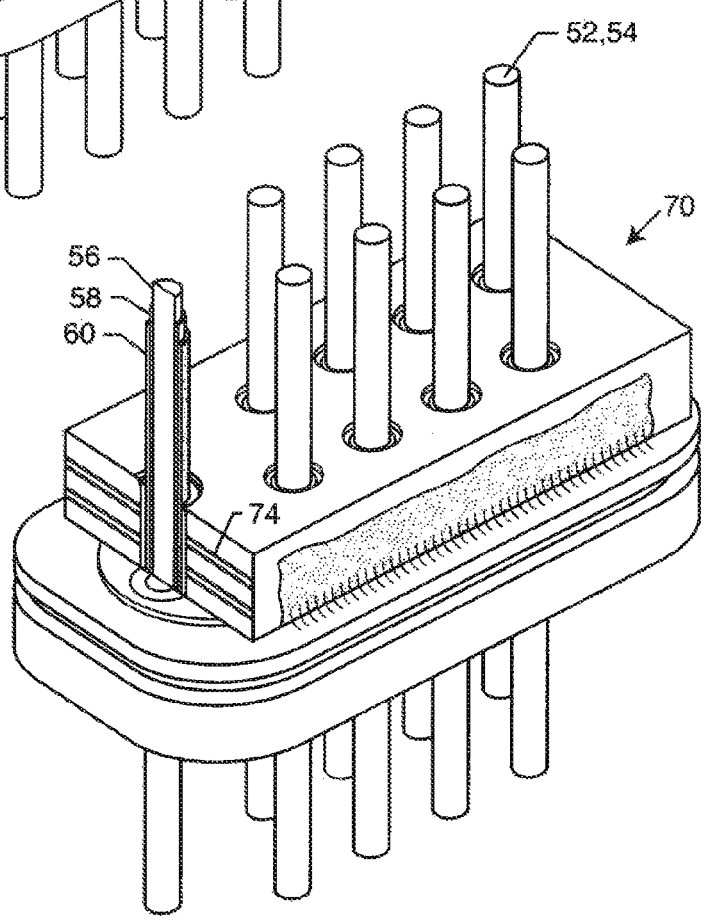
FIG. 17 is similar to FIG. 16, and includes a partial sectional view taken generally along the line 17-17 of FIG. 16.

FIG. 17 is similar to FIG. 16 and includes a cutaway cross-sectional view taken generally along the line 17-17 of FIG. 16, showing the attachment of the internal ground electrode plates 74 of the capacitor 70 to the conductive shield 60. In this case, dual ground electrode plates 74 are shown in accordance with U.S. Pat. No. 5,978,204.

FIG. 18 illustrates a reinforced polyimide tubing 106. As shown in FIG. 19, the typical construction consists of a substrate layer 108, a braided or coiled metallic layer 110 and an exterior layer 112. The substrate 108 and exterior layer 112 are insulative wherein the embedded braided or coiled layer 110 is a conductive metal. The most common braid coil 110 material is 304V stainless steel. Other metallic materials can also be used. The embedded braid coil 110 accomplishes RF shielding of the RF telemetry pin antenna 56 in accordance with the present invention. Inside diameters (ID) can be as small as 0.010 inches. FEP and PTFE coatings can be added to the ID, outside diameter (OD), or both to enhance slickness to make it easy to slide the reinforced polyimide tubing 106 over the RF telemetry pin antenna 56. Grounding, (otherwise known as shield termination) is preferable to the termination 88 of the inside diameter ground electrode plates 74 of the feedthrough capacitor 70 (or the other grounding methods as previously described herein). This would involve chemically or mechanically removing a small amount of the exterior layer 112 in the area marked "b" to expose the actual embedded metallic braid or coil material 110. An electrical connection 86 comprised of a conductive thermal setting adhesive or the like would be used to make connection to the exposed braid 110. A similar procedure can be used to attach the ground circuitry to the circuit board or substrate of the AIMD (ref. FIG. 7, attachment point 98).

FIG. 20 illustrates an alternative embodiment wherein a commercially available insulation tube 58 is slipped over the RF telemetry pin antenna 56. Then, a solid metal tube 114, such as a soft copper tube, is slipped over the insulation tube 58 as shown.

FIGS. 21 and 22 are similar to FIG. 20 except that the solid metal tube 114 is replaced by wound wire strands 116 or wrapped foil 150, respectively, or other equivalent materials which are commonly used in shielded cables world wide.

Figure 23:
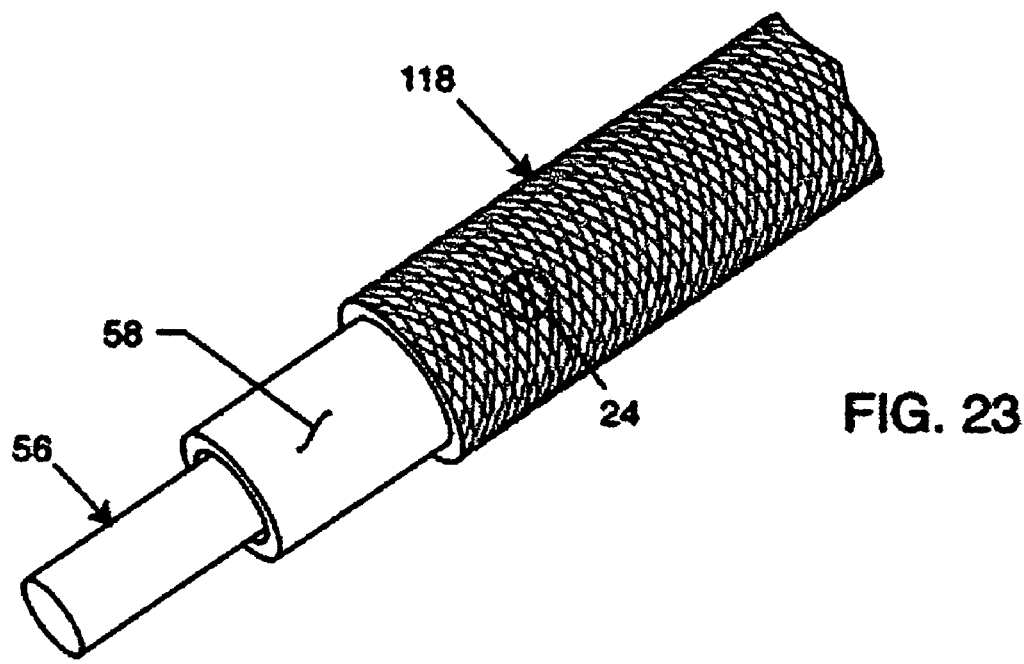
FIG. 23 is a perspective view similar to FIG. 21, illustrating use of a braided shield wire instead of a wound shield wire.
Figure 24:
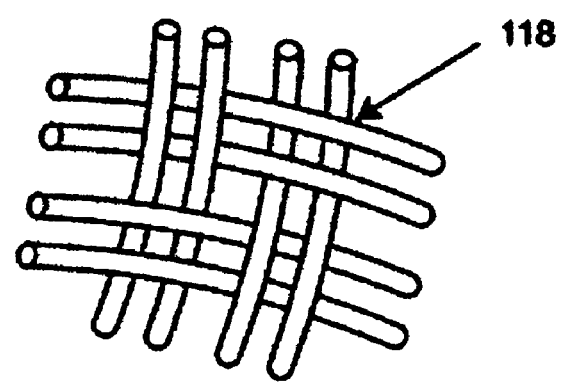
FIG. 24 is an enlarged, fragmented perspective view of the area indicated by the number 24 in FIG. 23, showing how the braided wires interweave.

FIG. 23 shows a cross braided shield wire 118 instead of a wound shield wire (compare to FIG. 21). The cross braid shield 118 is shown in more detail in FIG. 24, wherein one can see how the braided wires interweave.

Figure 25:
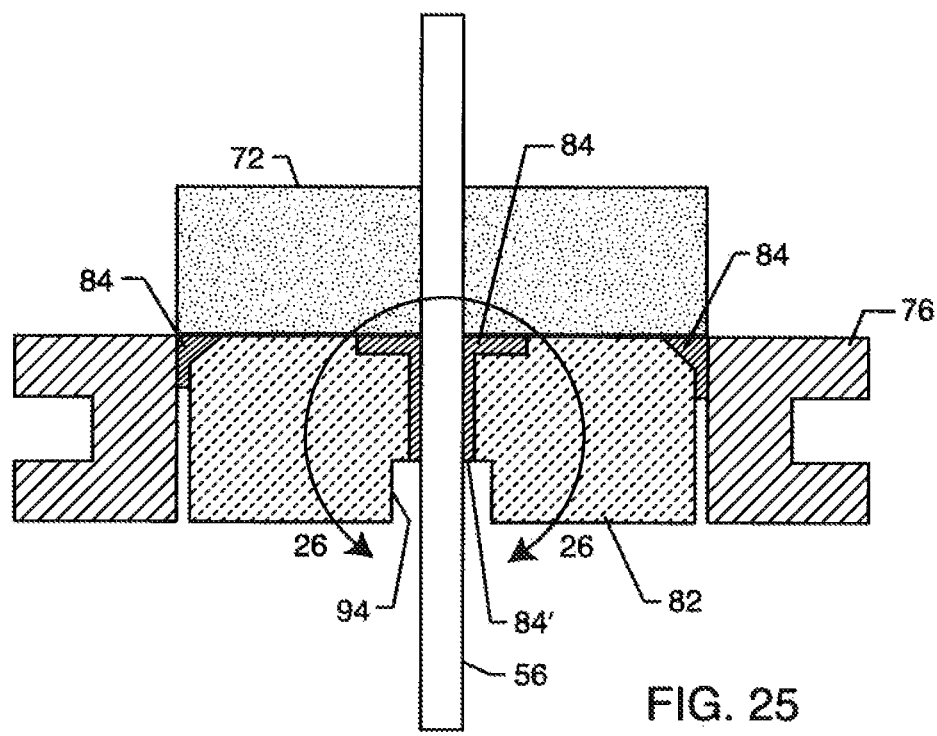
FIG. 25 is a cross-section taken generally along the line 25-25 of FIG. 10.

FIG. 25 is a cross-section taken generally along line 25-25 of FIG. 10. This illustrates an alternative method of using a counterbore 94 to control the depth of gold braze penetration 84'. As mentioned before, it is important to control the amount of gold braze penetration so that too much distributed capacitance is prevented from building up between the RF telemetry pin antenna 56 and the surrounding metallic ferrule 76. Because insulator 82 generally has a relatively higher dielectric constant than air, this is important. It is also important to not only limit the amount of distributive capacitance, but also to make sure that it is consistent so that proper transmission line matching could be made to the RF telemetry circuitry and antenna.

Figure 26:
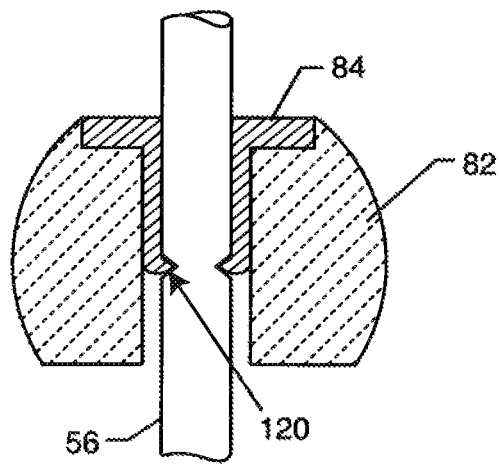
FIG. 26 is an enlarged, fragmented cross-sectional view taken of the area 26-26 in FIG. 25, illustrating the use of a notch in the lead wire to limit the flow of braze material down the lead wire.
Figure 27:
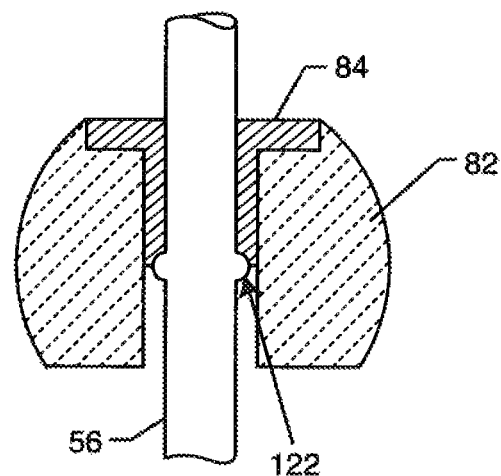
FIG. 27 is a sectional view similar to FIG. 26, illustrating the use of a swadge area or bump on the lead wire to control the flow of adjacent gold braze material.

In like manner, FIGS. 26 and 27 also show alternative methods of controlling the gold braze penetration. FIG. 26 illustrates a novel notch 120 in the lead wire to interfere with the capillary action and prevent the gold braze from flowing. In a similar manner, the swadge area 122 or bump of FIG. 27 accomplishes the same thing. It will be obvious to those skilled in the art that there are a number of ways to deliberately halt and control the penetration of the gold braze in the high temperature vacuum-brazing furnace.

Figure 28:
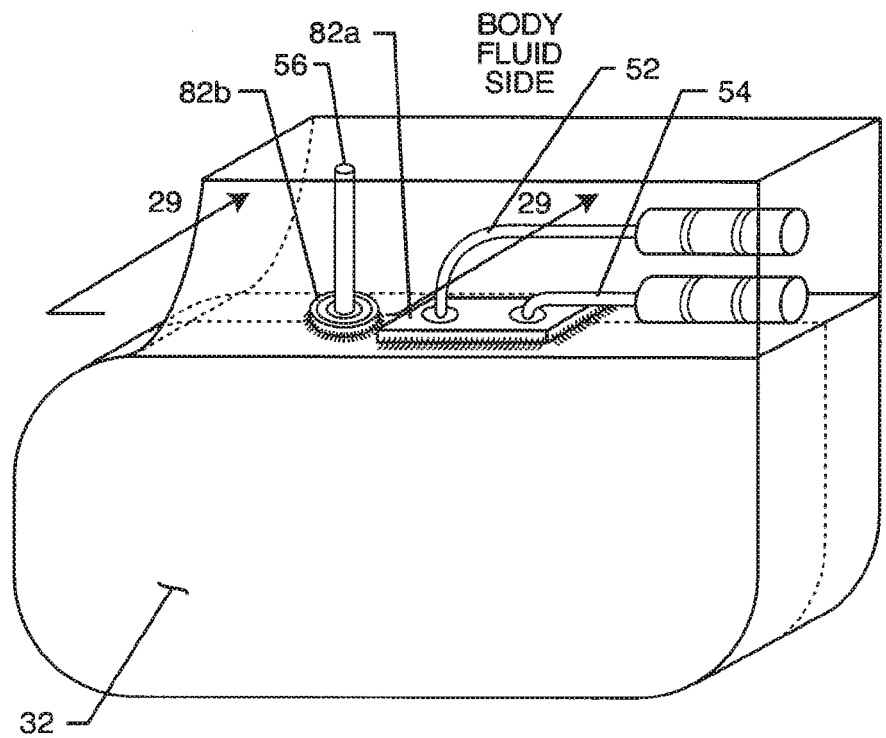
FIG. 28 is an isometric drawing of an active implantable medical device embodying the novel shield for an RF telemetry pin of the present invention.

FIG. 28 is an isometric view of an AIMD such as a cardiac pacemaker wherein the hermetic seal or insulator 82b disposed around the RF terminal pin 56 is shown separate and distinct from one or more other hermetic seals or insulators 82a that encompass lead wires 52 and 54 which connect to body tissue. A unipolar RF telemetry pin 56 is shown in FIG. 28.

Figure 29:
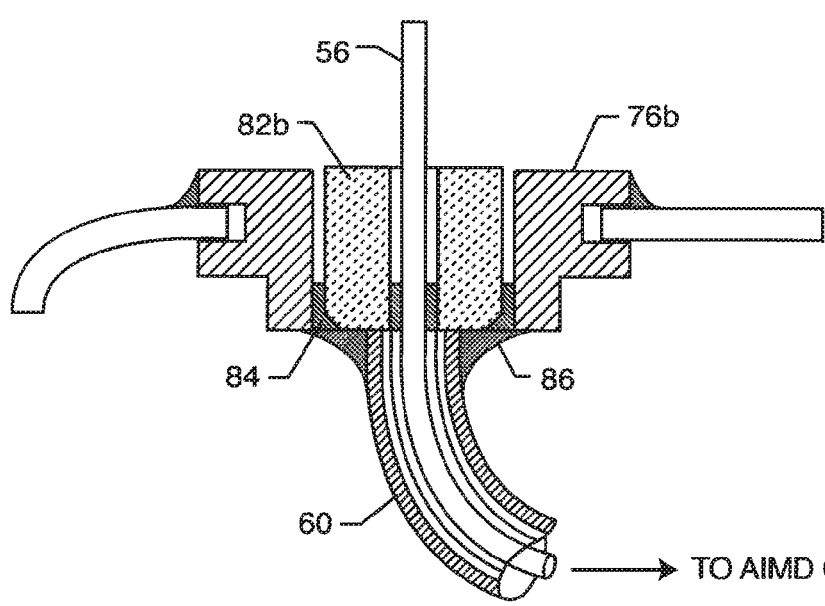
FIG. 29 is a cross-sectional view taken generally along line 29-29 of FIG. 28.

FIG. 29 is a cross-sectional view taken generally along line 29-29 from FIG. 28. The RF telemetry pin 56 is shown routed to internal circuits of the AIMD. Also shown is the novel shield 60 of the present invention which has been electrically connected using material 86 to the hermetic terminal gold braze 84. Gold braze 84 connects the ferrule 76b to the insulator 82b. Although not shown in this Figure, lead wires 52, 54 pass through an insulator and ferrule separate and distinct from the ferrule 76b and the insulator 82b associated with the RF telemetry pin 56. In this way the shield 60 has been grounded to the overall housing of the AIMD. This forms a continuous electromagnetic shield or ground plane such that any EMI that has been superimposed on the RF telemetry pin 56 cannot escape from and re-radiate to sensitive circuits within the AIMD. Any of the shields 60 of the present invention can be incorporated along with said unipolar terminal to achieve the desired shielding. It will also be obvious that a number of brackets could be used to replace the electrical connecting material 86 in accordance with the present invention.

One can also see that the lead wires 52 and 54 are associated with internal electronic circuits of the AIMD. As previously discussed, these lead wires are designed to be routed to deliver appropriate stimulation pulses to body tissue. The same lead wires are also used to sense biological functions in the body. For example, in the case of cardiac pacemaker, the lead wires 52 and 54 could be used to sense cardiac rhythms. When such cardiac rhythms are not normal, the lead wires 52 and 54 can become pacing leads thereby providing electrical stimulus to cardiac tissue to restore sinus rhythm. Prior art EMI filters have been described herein wherein feedthrough capacitors can be associated with such lead wires to decouple undesirable electromagnetic interference before it enters into the inside of the AIMD and can disrupt its electronic circuitry. An alternative to the use of a feedthrough capacitor is to use the principles of the present invention to shield the lead wires 52 and 54 on the inside of the housing. This would be a shield assembly which is identical to that shown in FIG. 29, except that the shield assembly 60 would also be placed over the lead wires 52 and 54, including insulation tubing. In this way, the lead wires 52 and 54 could be safely routed to electronic circuits within the AIMD without the potential for EMI to re-radiate or couple to other areas within the AIMD. This would require the use of EMI filters disposed at the circuit board or substrate at the terminal end of said lead wires 52 and 54. That is, EMI would still try to enter the pacemaker sensing circuits. However, it is well known in the prior art that electronic, passive or low pass filters could be used at that point to prevent EMI from entering into the pacemaker sense circuits.

Although various embodiments have been described in detail for purposes of illustration, various modifications may be made without departing from the scope and spirit of the invention.

What is claimed is:

1. A terminal assembly for an active implantable medical device (AIMD), comprising:
   a) a housing for the AIMD, the housing having an outboard body fluid side and an inboard side;
   b) a hermetic feedthrough terminal comprising a ferrule hermetically sealed to the housing and supporting an insulative material sealing between at least one conductive leadwire and an inner surface of the ferrule;
   c) at least one capacitor mounted to the feedthrough terminal and comprising spaced apart active and ground electrode plates encased in a dielectric material, wherein the at least one leadwire extends from the feedthrough terminal and is electrically connected to the active electrode plates of the capacitor with the ground electrode plates being electrically connected to the ferrule and the AIMD housing;
   d) an electrically conductive pin extending through the AIMD housing in non-conductive relation thereto, wherein the conductive pin extends from a proximal pin portion that is electrically connected to an electronic circuit board or substrate disposed within the housing remote from the feedthrough terminal to a distal portion that extends through the insulative material of the feedthrough terminal in non-conductive relation to the body fluid side and wherein the conductive pin is not electrically connected to either the active or ground electrode plates of the capacitor; and
   e) a conductive shield comprising a substantially continuous covering that is coaxially disposed around an outer perimeter of the conductive pin in non-conductive relationship therewith, but that conductively extends along the length of the conductive pin from a proximal shield end adjacent to the circuit board or substrate to a distal shield end electrically connected to the ground electrode plates, the ferrule and the AIMD housing.

2. The assembly of claim 1 wherein the conductive shield extends along the length of the conductive pin from the proximal shield end electrically connected to a ground plane of the circuit board or substrate to the distal shield end electrically connected to the capacitor ground electrode plates, the ferrule and the AIMD housing.

3. The assembly of claim 2 wherein the housing comprises the ground plane.

4. The assembly of claim 3 wherein the ground plane comprises the conductive ferrule.

5. The assembly of claim 1, including a conductive metal coating covering at least a portion of the outer surface of the feedthrough capacitor, wherein the metal coating is conductively connected to the ground electrode plates and the housing.

6. The assembly of claim 5 wherein the metal coating of the feedthrough capacitor is conductively connected to the conductive shield of the conductive pin.

7. The assembly of claim 6, wherein the metal coating is conductively connected to the conductive shield by a solder, a braze, or a thermal setting conductive adhesive.

8. The assembly of claim 1, further comprising a conductive metal frame covering a portion of the outer surface of the feedthrough capacitor and conductively connected to the housing and the conductive shield of the conductive pin.

9. The assembly of claim 1, wherein the AIMD is selected from the group consisting of a cardiac pacemaker, a cardiac sensing system, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, and a prosthetic device.

10. The assembly of claim 1, further comprising an insulation tube between the conductive pin and the conductive shield.

11. The assembly of claim 10, wherein the insulation tube is selected from the group consisting of of Kovar, a polyimide, Teflon, silicone, and a conductive heat shrink tubing.

12. The assembly of claim 1, wherein the conductive shield is selected from the group consisting of gold, copper, and nickel.

13. The assembly of claim 1, wherein the conductive shield is selected from the group consisting of a solid metal tube, a wound wire tube, a braided wire tube or a wrapped foil tube.

14. The assembly of claim 13, wherein the wound wire or braided wire material comprises 304V stainless steel.

15. The assembly of claim 1 wherein the circuit board or substrate includes a wire bond pad, and wherein the proximal pin portion is conductively connected to the wire bond pad of the circuit board or substrate by a thermal bond, an ultrasonic bond, a solder or a conductive adhesive.

16. The assembly of claim 15, further comprising a second wire bond pad on the substrate conductively connected to the conductive shield of the conductive pin.

17. The assembly of claim 16, wherein the proximal shield end is conductively connected to the second wire bond pad by a thermal bond, an ultrasonic bond, a solder, or a conductive adhesive.

18. The assembly of claim 1, further comprising a counterbore in the insulative material of the feedthrough terminal, the counterbore being disposed around the conductive pin.

19. The assembly of claim 18, further comprising a notch or swage on the conductive pin inside the feedthrough terminal.

20. The assembly of claim 5, further comprising an exterior insulation layer over the conductive shield of the conductive pin.

21. The assembly of claim 20, wherein the exterior insulation layer comprises polyimide tubing.

22. The assembly of claim 20, wherein the conductive shield is conductively connected to the ground electrode plates by removing a portion of the exterior insulation layer at the proximal shield end.

23. The assembly of claim 1 wherein the capacitor is supported on the feedthrough terminal adjacent to the inboard side of the AIMD housing.

24. A terminal assembly for an active implantable medical device (AIMD), comprising:
 a) a housing for the AIMD, the housing having an outboard body fluid side and an inboard side;
 b) a hermetic feedthrough terminal comprising a ferrule hermetically sealed to the housing and supporting an insulative material sealing between at least one conductive leadwire and an inner surface of the ferrule;
 c) at least one capacitor mounted to the feedthrough terminal and comprising spaced apart active and ground electrode plates encased in a dielectric material, wherein the at least one leadwire extends from the feedthrough terminal and is electrically connected to the active electrode plates of the capacitor with the ground electrode plates being electrically connected to the ferrule and the AIMD housing;
 d) an electrically conductive pin extending through the housing in non-conductive relation thereto, wherein the conductive pin extends from a proximal pin portion that is electrically connected to a radio frequency (RF) detection circuit mounted on a circuit board or substrate disposed within the housing remote from the feedthrough terminal to a distal portion that extends through the insulative material of the feedthrough terminal in a non-conductive relation to the body fluid side and wherein the conductive pin is not electrically connected to either the active or ground electrode plates of the capacitor;
 e) a conductive shield comprising a substantially continuous covering that is coaxially disposed around an outer perimeter of the conductive pin in non-conductive relationship therewith, but that conductively extends along the length of the conductive pin from a proximal shield end electrically connected a ground plane of the circuit board or substrate to a distal shield end electrically connected to the ground electrode plates, the ferrule and the AIMD housing.

25. A terminal assembly for an active implantable medical device (AIMD), comprising:
 a) a housing for the AIMD, the housing having an outboard body fluid side and an inboard side;
 b) a hermetic feedthrough terminal comprising an insulative material sealing between at least one conductive leadwire and an inner surface of an opening in the housing;
 c) at least one capacitor mounted to the feedthrough terminal and comprising spaced apart active and ground electrode plates encased in a dielectric material, wherein the at least one leadwire extends from the feedthrough terminal and is electrically connected to the active electrode plates of the capacitor with the ground electrode plates being electrically connected to the AIMD housing;
 d) an electrically conductive pin extending through the AIMD housing in non-conductive relation thereto, wherein the conductive pin extends from a proximal pin portion that is electrically connected to an electronic circuit board or substrate disposed within the housing remote from the feedthrough terminal to a distal portion that extends through the insulative material of the feedthrough terminal in non-conductive relation to the body fluid side and wherein the conductive pin is not electrically connected to either the active or around electrode plates of the capacitor; and
 e) a conductive shield comprising a substantially continuous covering that is coaxially disposed around an outer perimeter of the conductive pin in non-conductive relationship therewith, but that conductively extends along the length of the conductive pin from a proximal shield end adjacent to the circuit board or substrate to a distal shield end electrically connected to the ground electrode plates and the AIMD housing.

* * * * *